United States Patent
Lidor-Hadas et al.

(10) Patent No.: US 7,619,117 B1
(45) Date of Patent: Nov. 17, 2009

(54) RASAGILINE FORMULATIONS AND PROCESSES FOR THEIR PREPARATION

(75) Inventors: Ramy Lidor-Hadas, Kfar Saba (IL); Eliezer Bahar, Tel Aviv (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

(21) Appl. No.: 12/283,022

(22) Filed: Sep. 8, 2008

Related U.S. Application Data

(62) Division of application No. 11/634,916, filed on Dec. 5, 2006, now Pat. No. 7,572,834.

(60) Provisional application No. 60/742,823, filed on Dec. 6, 2005.

(51) Int. Cl.
*C07C 209/74* (2006.01)
*C07C 211/42* (2006.01)

(52) U.S. Cl. ................................ 564/404; 564/308

(58) Field of Classification Search ............... None
See application file for complete search history.

(56) References Cited

U.S. PATENT DOCUMENTS

| | | |
|---|---|---|
| 5,387,612 A | 2/1995 | Youdim et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,668,181 A | 9/1997 | Youdim et al. |
| 5,744,500 A | 4/1998 | Youdim et al. |
| 5,786,390 A | 7/1998 | Youdim et al. |
| 5,891,923 A | 4/1999 | Youdim et al. |
| 6,126,968 A | 10/2000 | Peskin et al. |
| 6,277,886 B1 | 8/2001 | Levy et al. |
| 6,316,504 B1 | 11/2001 | Youdim et al. |
| 6,462,222 B1 | 10/2002 | Chorev et al. |
| 6,630,514 B2 | 10/2003 | Youdim et al. |
| 6,635,667 B2 | 10/2003 | Thomas |
| 6,956,060 B2 | 10/2005 | Youdim et al. |
| 7,491,847 B2 | 2/2009 | Frenkel |
| 2004/0010038 A1 | 1/2004 | Blaugrund et al. |
| 2004/0052843 A1 | 3/2004 | Lerner et al. |
| 2004/0127577 A1 | 7/2004 | Blaugrund et al. |
| 2006/0018957 A1 | 1/2006 | Lerner et al. |
| 2006/0094783 A1 | 5/2006 | Youdim et al. |
| 2006/0188581 A1 | 8/2006 | Peskin |
| 2007/0100001 A1 | 5/2007 | Youdim et al. |
| 2007/0112217 A1 | 5/2007 | Frenkel et al. |
| 2007/0232700 A1 | 10/2007 | Blaugrund et al. |
| 2008/0146676 A1 | 6/2008 | Frenkel et al. |
| 2008/0161408 A1 | 7/2008 | Frenkel et al. |

FOREIGN PATENT DOCUMENTS

| | | |
|---|---|---|
| EP | 0538134 | 4/1993 |
| EP | 0436492 | 6/1994 |
| WO | 9511016 | 4/1995 |
| WO | 9518617 | 7/1995 |
| WO | 9637199 | 11/1996 |
| WO | 9712583 | 4/1997 |
| WO | 9802152 | 1/1998 |
| WO | 03072055 | 9/2003 |
| WO | 2004045515 | 6/2004 |
| WO | 06057912 | 11/2004 |
| WO | 2006014973 | 2/2006 |
| WO | 2008019871 | 2/2008 |
| WO | 2008131961 | 6/2008 |

OTHER PUBLICATIONS

Paquette et al., J. Org. Chem. (1998), 63(6), p. 2022-2030.*
Finberg et al. (1981) "Selective Irreversible Propargyl Derivative Inhibitors of Monoamine Oxidase (MAO) without the Cheese Effect" *Chem. Abstracts* 94:202499.
Finberg and Youdim (1985) "Modification of Blood Pressure and Nictitating Membrane Response to Sympathetic Amines by Selective Monoamine Oxidase Inhibitors" *Brit. J.Pharmac.* 85(2):541-546.
Finberg et al. (1985) "Modification of Blood Pressure and Nictitating Membrane Response to Sympathetic Amides by Selective Monoamide Oxidase Inhibitors, Types A and B, in the Cat" *Chem. Abstracts* 103:81618.
U.S. Appl. No. 11/595,726, filed Nov. 10, 2006, Youdim et al.
Mendlewicz and M.B.H. Youdim (1983) *Brit. J. Psychiat.* 142:508-511.
Youdim MBH, et al., "Rasagiline (N-propargyl-1R(+)-aminoindan), a selective and potent inhibitor of mitochondrial monoamine oxidase B", *Br. J. Pharmacol.*, 2001,132:500-6.

(Continued)

*Primary Examiner*—Brian J Davis
(74) *Attorney, Agent, or Firm*—John P. White; Cooper & Dunham LLP

(57) ABSTRACT

The subject invention provides a pharmaceutical composition comprising N-propargyl-1(R)-aminoindan mesylate; a pharmaceutically acceptable carrier; and greater than 0.7 ppm but less than 30 ppm in total of a compound having the structure:

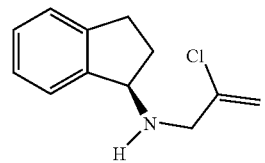

and any salts of the compound.

11 Claims, 5 Drawing Sheets

OTHER PUBLICATIONS

Youdim et al. in Handbook of Experimental Pharmacology vol. 90/I (1988) Chapter 3, Trendlenburg and Weiner, eds.
Youdim et al. (1984) *Progress in Medicinal Chemistry* 21:138-167.
U.S. Appl. No. 11/600,561, filed Nov. 15, 2006, Frenkel et al.
U.S. Appl. No. 11/634,916, filed Dec. 6, 2005, Sterling et al.
U.S. Appl. No. 11/791,684, filed May 24, 2007, Patashnik et al.
U.S. Appl. No. 12/002,082, filed Dec. 12, 2007, Anton Frenkel and Tamas Koltai.
Office Action issued Mar. 5, 2009 in the U.S. Appl. No. 12/183,105.
Office Action issued Mar. 24, 2009 in the U.S. Appl. No. 12/283,107.
Kirk-Othmer Encyclopedia of Chemical Technology (2005), John Willy & Sons, Inc. vol. 18, entry: Pharmaceuticals, p. 33, No. 11.
U.S. Appl. No. 12/223,794, filed Aug. 7, 2008, Poewe et al.
U.S. Appl. No. 12/283,946, filed Sep. 16, 2008, Lendvai et al.
U.S. Appl. No. 12/231,601, filed Sep. 3, 2008, Oron et al.
U.S. Appl. No. 12/283,105, filed Sep. 8, 2008, Sterling et al.
U.S. Appl. No. 12/283,107, filed Sep. 8, 2008, Sterling et al.
Scientific Discussion. (EMEA 2005), http://www.emea.europa.eu/humandocs/PDFs/EPAR/Azilet/528970en6.pdf, published Mar. 17, 2005, especially p. 9.
Office Action issued Jul. 11, 2008 in the U.S. Appl. No. 11/634,916.
Office Action issued May 2, 2008 in the U.S. Appl. No. 11/634,916.

\* cited by examiner

RASAGILINE FORMULATIONS AND PROCESSES FOR THEIR PREPARATION

This application is a divisional of U.S. patent application Ser. No. 11/634,916 filed Dec. 5, 2006, which claims benefit of U.S. Provisional Application No. 60/742,823, filed Dec. 6, 2005, the contents of all of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Rasagiline is a selective irreversible inhibitor of monoamine oxidase enzyme Type-B (MAO-B) and has the chemical name N-propargyl-1(R)-aminoindan ("(R)-PAI"). Its structural formula is:

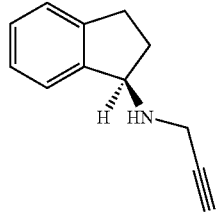

(R)-PAI is an active MAO-B inhibitor while the corresponding S-enantiomer ("(S)-PAI") shows extremely low MAO-B inhibitory activity (U.S. Pat. No. 6,316,504). It has also been found that (R)-PAI has a degree of selectivity for MAO-B inhibition surprisingly higher than that of the corresponding racemic form (U.S. Pat. No. 6,316,504). The fact that (R)-PAI is more active than the racemic mixture for the inhibition of MAO-B is a reflection of the extremely low activity of (S)-PAI for inhibition of MAO-B (U.S. Pat. No. 6,316,504).

Rasagiline, its salts, preparation and use for the treatment of Parkinson's disease, Alzheimer's Disease, memory disorders, stroke and other disorders have been the subject of numerous patents, including U.S. Pat. Nos. 5,387,612, 5,453,446, 5,457,133, 5,668,181, 5,576,353, 5,532,415, 5,599,991, 5,786,390, 5,519,061, 5,891,923, 5,744,500 and 6,316,504, the contents of which are hereby incorporated by reference. Rasagiline formulations are described in U.S. Pat. No. 6,126,968, the contents of which are also hereby incorporated by reference.

SUMMARY OF THE INVENTION

The subject invention provides a pharmaceutical composition comprising N-propargyl-1(R)-aminoindan mesylate; a pharmaceutically acceptable carrier; and greater than 0.7 ppm but less than 30 ppm in total of a compound having the structure:

and any salts of the compound.

The subject invention also provides a process for preparing a pharmaceutical product comprising N-propargyl-1(R)-aminoindan mesylate and a pharmaceutically acceptable carrier, wherein the pharmaceutical product has less than 30 ppm in total of N-2-propene-1-yl-2-chloro-(R)-aminoindan and any salts thereof, the process comprising
  a) obtaining a batch of N-propargyl-1(R)-aminoindan mesylate;
  b) determining the total amount of N-2-propene-1-yl-2-chloro-(R)-aminoindan and any salts thereof present in the batch; and
  c) preparing the pharmaceutical product from the batch only if the batch is determined to have less than 30 ppm in total of N-2-propene-1-yl-2-chloro-(R)-aminoindan and salts thereof.

The subject invention also provides a process for validating a batch of a pharmaceutical product containing N-propargyl-1(R)-aminoindan mesylate and at least one pharmaceutically acceptable carrier for distribution comprising
  a) subjecting a sample of the batch to stability testing;
  b) determining the total amount of N-2-propene-1-yl-2-chloro-(R)-aminoindan and any salts thereof in the sample of the batch after stability testing; and
  c) validating the batch for distribution only if the sample of the batch after stability testing contains less than 30 ppm in total of N-2-propene-1-yl-2-chloro-(R)-aminoindan and salts thereof.

The subject invention also provides a process of making a pharmaceutical composition comprising N-propargyl-1(R)-aminoindan mesylate and at least one pharmaceutically acceptable carrier, the process comprising admixing the N-propargyl-1(R)-aminoindan mesylate with the at least one pharmaceutically acceptable carrier, wherein the at least one pharmaceutically acceptable carrier is free of a chloride-containing compound.

The subject invention also provides a process for testing whether a sample contains an undesirable chlorinated N-allyl aminoindan which comprises determining whether the sample contains a compound having the structure:

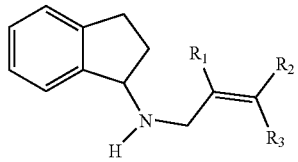

wherein one of $R_1$, $R_2$ or $R_3$ is Cl and the remainder are H, or a salt thereof.

The subject invention also provides an isolated compound having the structure:

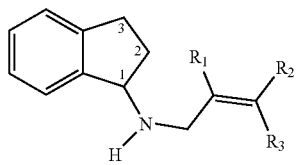

wherein one of $R_1$, $R_2$ or $R_3$ is Cl and the remainder are H, or a salt thereof, wherein the isolated compound is free of an N-propargyl-1-aminoindan or a salt thereof.

The subject invention also provides a compound having the structure:

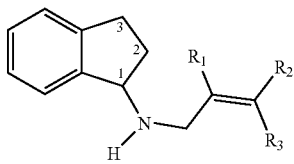

wherein one or more of the carbons is $^{13}$C, one of $R_1$, $R_2$ or $R_3$ is Cl and the remainder are H, or a salt thereof.

The subject invention also provides a composition comprising a compound having the structure:

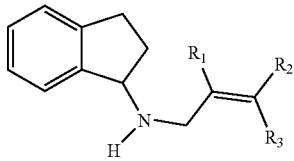

wherein one of $R_1$, $R_2$ or $R_3$ is Cl and the remainder are H, or a salt thereof; and a carrier, wherein the composition is free of an N-propargyl-1-aminoindan or a salt thereof.

The subject invention also provides a process of manufacturing N-2-propene-1-yl-3-chloro-cis-aminoindan, N-2-propene-1-yl-3-chloro-trans-aminoindan, or an enantiomer or a salt of any one thereof, comprising reacting a compound having the structure:

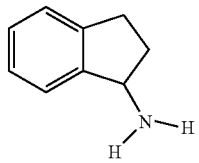

with 1,3-dichloropropene in the presence of a base and N,N-dimethylacetamide so as to produce the compound.

The subject invention also provides a process of manufacturing (1,2,3) $^{13}$C—N-2-propene-1-yl-2-chloro-aminoindan or an enantiomer or a salt thereof, comprising:
  a) heating a mixture of (1,2,3) $^{13}$C-aminoindan and a base in a first suitable solvent,
  b) adding 2,3-dichloro-1-propene to produce (1,2,3) $^{13}$C—N-propargyl-1-aminoindan,
  c) reacting the (1,2,3) $^{13}$C—N-propargyl-1-aminoindan of step b) with HCl in the presence of a second suitable solvent to produce the compound.

The subject invention also provides use of N-2-propene-1-yl-2-chloro-aminoindan, (1,2,3) $^{13}$C—N-2-propene-1-yl-2-chloro-aminoindan, N-2-propene-1-yl-3-chloro-cis-aminoindan, N-2-propene-1-yl-3-chloro-trans-aminoindan, or an enantiomer or a salt of any one thereof, as a reference standard to detect trace amounts of impurities in a pharmaceutical composition.

DETAILED DESCRIPTION

Figure 1:
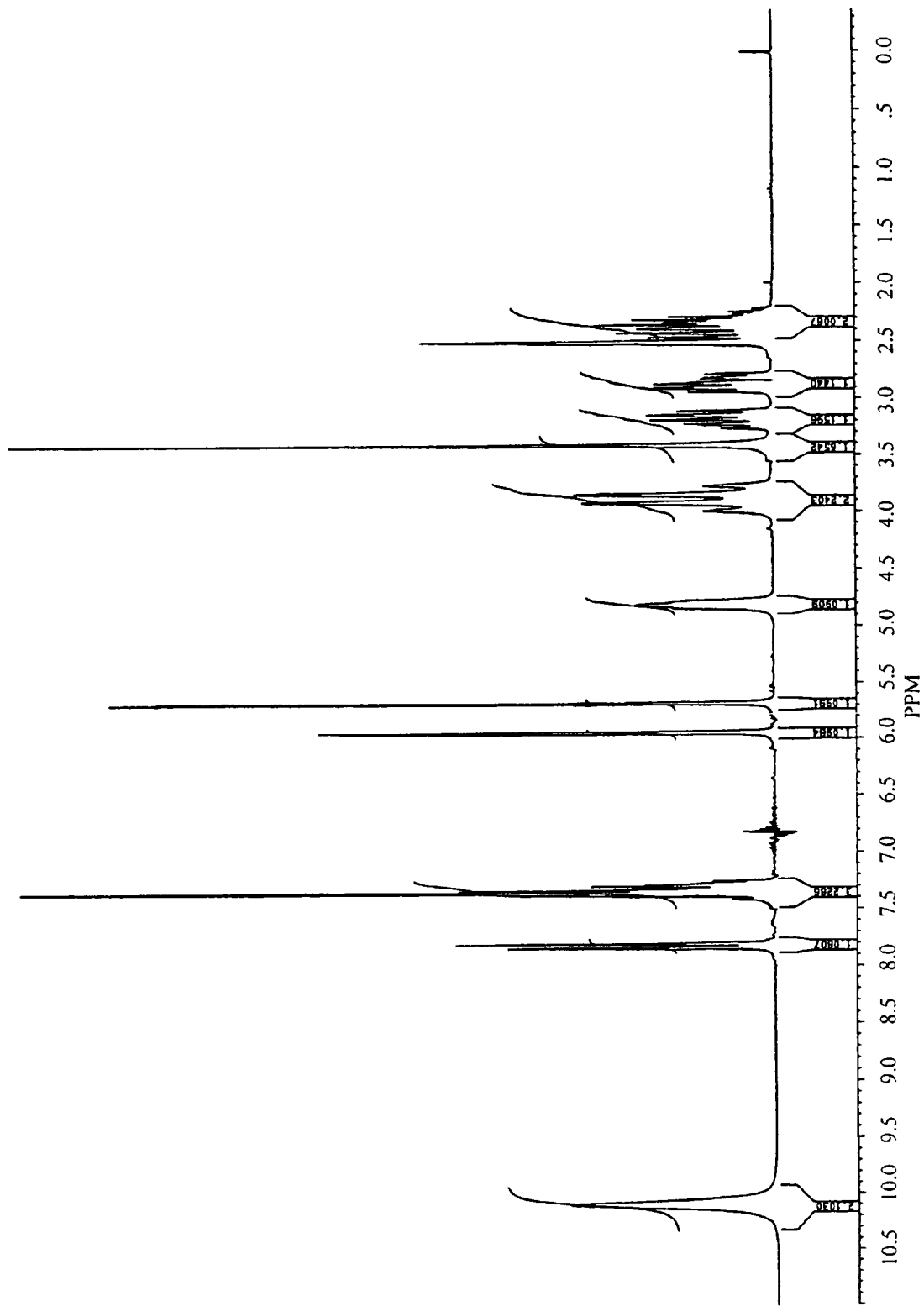
FIG. 1 $^1$H nuclear magnetic resonance (NMR) spectrum of a sample of N-2-propene-1-yl-2-chloroaminoindan hydrochloride obtained on a Bruker 200 MHz apparatus in DMSO-$d_6$.

The subject invention provides a pharmaceutical composition comprising N-propargyl-1(R)-aminoindan mesylate; a pharmaceutically acceptable carrier; and greater than 0.7 ppm but less than 30 ppm in total of a compound having the structure:

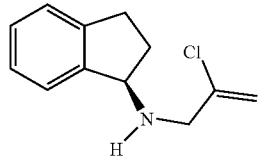

and any salts of the compound.

By greater than 0.7 ppm but less than 30 ppm it is meant that all tenth and integer unit amounts within the range are specifically disclosed as part of the invention. Thus, 0.7, 0.8, 0.9 and 1, 2, 3, 4, . . . 27, 28, 29 and 30 ppm unit amounts are included as embodiments of this invention.

In one embodiment, the pharmaceutical composition comprises greater than 1 ppm, greater than 2 ppm, greater than 3 ppm, greater than 4 ppm, greater than 5 ppm, greater than 6 ppm, or greater than 7 ppm in total of the compound and the salt of the compound.

In another embodiment, the pharmaceutically acceptable carrier does not include magnesium stearate.

In yet another embodiment, the pharmaceutically acceptable carrier comprises mannitol, starch, pregelatinized starch, colloidal silicon dioxide, stearic acid and/or talc.

In yet another embodiment, the pharmaceutical composition is free of maltodextrin, croscarmellose sodium, citric acid, lactose, glyceryl behenate and hydrogenated vegetable oil type I.

The subject invention also provides a process for preparing a pharmaceutical composition comprising N-propargyl-1 (R)-aminoindan mesylate and a pharmaceutically acceptable carrier, wherein the pharmaceutical product has less than 30 ppm in total of N-2-propene-1-yl-2-chloro-(R)-aminoindan and any salts thereof, the process comprising
  a) obtaining a batch of N-propargyl-1(R)-aminoindan mesylate;
  b) determining the total amount of N-2-propene-1-yl-2-chloro-(R)-aminoindan and any salts thereof present in the batch; and
  c) preparing the pharmaceutical product from the batch only if the batch is determined to have less than 30 ppm in total of N-2-propene-1-yl-2-chloro-(R)-aminoindan and salts thereof.

In an embodiment of the process, the pharmaceutical composition is prepared from the batch if it contains a total amount of greater than 1 ppm, greater than 2 ppm, greater than 3 ppm, greater than 4 ppm, greater than 5 ppm, greater than 6 ppm, or greater than 7 ppm of N-2-propene-1-yl-2-chloro-(R)-aminoindan and salts thereof.

In another embodiment of the process, the pharmaceutical composition is prepared from the batch only if it contains a total amount of less than 7 ppm, less than 6 ppm, less than 5 ppm, less than 4 ppm, less than 3 ppm, less than 2 ppm, or less than 1 ppm of N-2-propene-1-yl-2-chloro-(R)-aminoindan and salts thereof.

In yet another embodiment of the process, the step of determining, the amount is determined using a measurement of mass, ultraviolet absorption, refractive index, ionization or voltammogram.

The subject invention also provides a process for validating a batch of a pharmaceutical product containing N-propargyl-1(R)-aminoindan mesylate and at least one pharmaceutically acceptable carrier for distribution comprising a) subjecting a sample of the batch to stability testing;
b) determining the total amount of N-2-propene-1-yl-2-chloro-(R)-aminoindan and any salts thereof in the sample of the batch after stability testing; and
c) validating the batch for distribution only if the sample of the batch after stability testing contains less than 30 ppm in total of N-2-propene-1-yl-2-chloro-(R)-aminoindan and salts thereof.

In an embodiment of the process, the batch is validated if the sample of the batch after stability testing contains a total amount greater than 0.7 ppm, greater than 1 ppm, greater than 2 ppm, greater than 3 ppm, or greater than 4 ppm of N-2-propene-1-yl-2-chloro-(R)-aminoindan and salts thereof.

In another embodiment of the process, the batch is validated only if the sample of the batch after stability testing contains a total amount less than 4 ppm, less than 3 ppm, less than 2 ppm, less than 1 ppm, or less than 0.7 ppm of N-2-propene-1-yl-2-chloro-(R)-aminoindan and salts thereof.

In yet another embodiment, in the step of determining, the amount is determined using a measurement of mass, ultraviolet absorption, refractive index, ionization or voltammogram.

The subject invention also provides a process of making a pharmaceutical composition comprising N-propargyl-1(R)-aminoindan mesylate and at least one pharmaceutically acceptable carrier, the process comprising admixing the N-propargyl-1(R)-aminoindan mesylate with the at least one pharmaceutically acceptable carrier, wherein the at least one pharmaceutically acceptable carrier is free of a chloride-containing compound.

In an embodiment of the process, the at least one pharmaceutically acceptable carrier does not include magnesium stearate.

In another embodiment of the process, the pharmaceutical acceptable carrier comprises mannitol, starch, pregelatinized starch, colloidal silicon dioxide, stearic acid and/or talc.

In yet another embodiment of the process, the pharmaceutical composition is free of maltodextrin, croscarmellose sodium, citric acid, lactose, glyceryl behenate and hydrogenated vegetable oil type I.

The subject invention also provides a process for testing whether a sample contains an undesirable chlorinated N-allyl aminoindan which comprises determining whether the sample contains a compound having the structure:

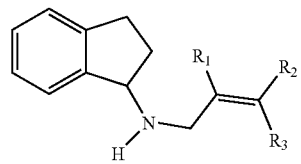

wherein one of $R_1$, $R_2$ or $R_3$ is Cl and the remainder are H, or a salt thereof. Specifically, the subject invention provides a process for testing whether a sample contains any of specific structures described herein.

The subject invention also provides an isolated compound having the structure:

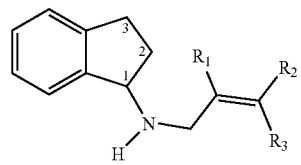

wherein one of $R_1$, $R_2$ or $R_3$ is Cl and the remainder are H, or a salt thereof, wherein the isolated compound is free of an N-propargyl-1-aminoindan or a salt thereof.

In an embodiment, the compound has the structure:

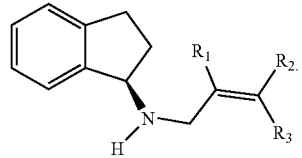

In another embodiment, the compound has the structure:

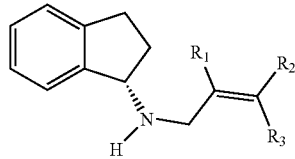

In another embodiment, the compound has the structure:

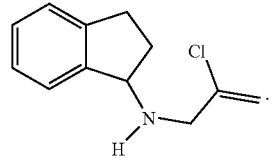

In another embodiment, the compound has the structure:

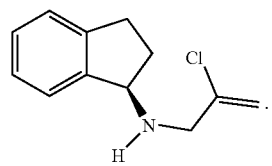

In another embodiment, the compound has the structure:

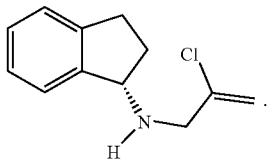

In another embodiment, the compound has the structure:

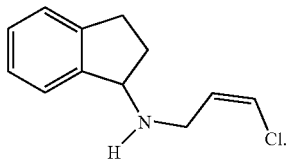

In another embodiment, the compound has the structure:

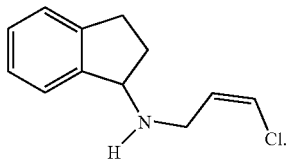

In another embodiment, the compound has the structure:

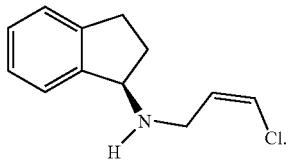

In another embodiment, the compound has the structure:

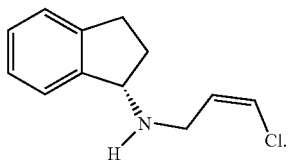

In another embodiment, the compound has the structure:

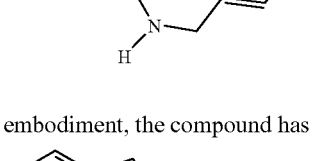

In another embodiment, the compound has the structure:

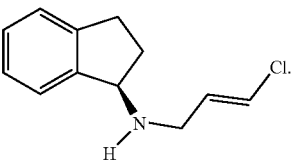

In a further embodiment of the compound, one or more of the carbons is $^{13}C$.

In yet a further embodiment of the compound, the $^{13}C$ is at positions 1, 2 and 3.

The subject invention also provides a compound having the structure:

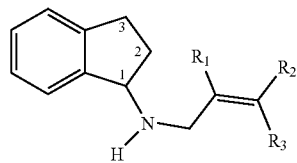

wherein one or more of the carbons is $^{13}C$, one of $R_1$, $R_2$ or $R_3$ is Cl and the remainder are H, or a salt thereof.

In an embodiment of the compound, the $^{13}C$ is at positions 1, 2 and 3.

In another embodiment, the compound has the structure:

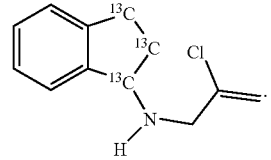

In another embodiment, the compound has the structure:

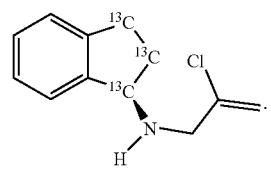

In another embodiment, the compound has the structure:

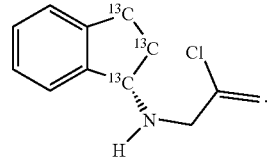

In another embodiment, the compound has the structure:

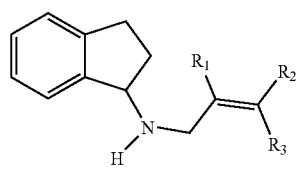

wherein one of $R_1$, $R_2$ or $R_3$ is Cl and the remainder are H, or a salt thereof; and a carrier, wherein the composition is free of an N-propargyl-1-aminoindan or a salt thereof.

The subject invention also provides a process of manufacturing N-2-propene-1-yl-3-chloro-cis-aminoindan, N-2-propene-1-yl-3-chloro-trans-aminoindan, or an enantiomer or a salt of any one thereof, comprising reacting a compound having the structure:

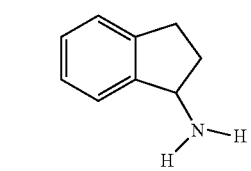

with 1,3-dichloropropene in the presence of a base and N,N-dimethylacetamide so as to produce the compound.

In an embodiment of the process, the base is $K_2CO_3$.

The subject invention also provides a process of manufacturing N-2-propene-1-yl-2-chloro-aminoindan, (1,2,3) $^{13}C$—N-2-propene-1-yl-2-chloro-aminoindan, N-2-propene-1-yl-3-chloro-cis-aminoindan, or an enantiomer or a salt of any one thereof, comprising reacting N-propargyl-1-aminoindan with hydrochloric acid in the presence of a suitable solvent so as to produce the compound.

In an embodiment of the process, the solvent is a mixture of toluene and water.

The subject invention also provides a process of manufacturing (1,2,3) $^{13}C$—N-2-propene-1-yl-2-chloro-aminoindan or an enantiomer or a salt thereof, comprising:

a) heating a mixture of (1,2,3) $^{13}C$-aminoindan and a base in a first suitable solvent, b) adding 2,3-dichloro-1-propene to produce (1,2,3) $^{13}C$—N-propargyl-1-aminoindan, c) reacting the (1,2,3) $^{13}C$—N-propargyl-1-aminoindan of step b) with HCl in the presence of a second suitable solvent to produce the compound.

In an embodiment of the process, the base is $K_2CO_3$.

In another embodiment of the process, the first suitable solvent is acetonitrile.

In another embodiment of the process, the second suitable solvent is ether.

In yet another embodiment, the process further comprises recovering the compound so produced.

The subject invention also provides use of N-2-propene-1-yl-2-chloro-aminoindan, (1,2,3) $^{13}C$—N-2-propene-1-yl-2-chloro-aminoindan, N-2-propene-1-yl-3-chloro-cis-aminoindan, N-2-propene-1-yl-3-chloro-trans-aminoindan, or an enantiomer or a salt of any one thereof, as a reference standard to detect trace amounts of impurities in a pharmaceutical composition.

In one embodiment, the impurity is a by-product. In another embodiment, the impurity is a degradant.

The (R) enantiomer forms of the compounds of the invention are referred to, for example, as follows: N-2-propene-1-yl-2-chloro-(R)-aminoindan, (1,2,3) $^{13}C$—N-2-propene-1-yl-2-chloro-(R)-aminoindan, N-2-propene-1-yl-3-chloro-cis-(R)-aminoindan and N-2-propene-1-yl-3-chloro-trans-(R)-aminoindan; also referred to as N-(2-chloroallyl)-1-(R)-aminoindan, (1,2,3) $^{13}C$—N-2-propene-1-yl-2-chloro-(R)-aminoindan, cis-N-(3-chloroallyl)-1-(R)-aminoindan and trans-N-(3-chloroallyl)-1-(R)-aminoindan (referred to hereinafter as 2-chloro-AAI, (1,2,3) $^{13}C$-2-chloro-AAI, cis-3-chloro-AAI and trans-3-chloro-AAI, respectively).

It will be noted that the structure of the compounds of this invention includes an asymmetric carbon atom and thus the compounds occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

It will also be noted that any notation of a carbon in structures throughout this application, when used without further notation, are intended to represent all isotopes of carbon, such as $^{12}C$ or $^{13}C$. Furthermore, any compounds containing $^{13}C$ may specifically have the structure of any of the compounds disclosed herein.

A characteristic of a compound refers to any quality that a compound exhibits, e.g., peaks or retention times, as determined by $^1H$ nuclear magnetic spectroscopy, mass spectroscopy, infrared, ultraviolet or fluorescence spectrophotometry, gas chromatography, thin layer chromatography, high performance liquid chromatography, elemental analysis, Ames test, dissolution, stability and any other quality that can be determined by an analytical method.

Once the characteristics of a compound are known, the information can be used to, for example, screen or test for the presence of the compound in a sample.

As used herein, a "pharmaceutically acceptable" carrier or excipient is one that is suitable for use with humans and/or animals without undue adverse side effects (such as toxicity, irritation, and allergic response) commensurate with a reasonable benefit/risk ratio.

Specific examples of pharmaceutical acceptable carriers and excipients that may be used to formulate oral dosage forms are described, e.g., in U.S. Pat. No. 6,126,968 to Peskin et al., issued Oct. 3, 2000. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

As used herein, "drug substance" refers to the active ingredient in a drug product, which provides pharmacological activity or other direct effect in the diagnosis, cure, mitigation, treatment, or prevention of disease, or to affect the structure or any function of the body of man or animals.

As used herein, "drug product" refers to the finished dosage form containing the drug substance as well as at least one pharmaceutically acceptable carrier.

As used herein, a composition that is "free" of a chemical entity means that the composition contains, if at all, an unavoidable level of the chemical entity but no more.

As used herein, "chloride-containing compound" refers to any compound containing at least one chloride ion (e.g., HCl).

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life.

Propargylated aminoindan refers to a compound having an aminoindan moiety with a propargyl substituent on the nitrogen atom, whether or not there exist any other substituents.

Specific salts provided by this invention are the mesylate, maleate, fumarate, tartrate, hydrochloride, hydrobromide, esylate, p-toluenesulfonate, benzoate, acetate, phosphate and sulfate salts.

For the preparation of pharmaceutically acceptable acid addition salts of the compounds of the invention, the free base can be reacted with the desired acids in the presence of a suitable solvent by conventional methods. Similarly, an acid addition salt may be converted to the free base form in a known manner.

U.S. Pat. No. 6,126,968, the entire contents of which are incorporated herein by reference, disclosed that the stability of formulations comprising PAI can be significantly improved by the incorporation of relatively large amounts of certain alcohols. In particular, the alcohol is selected from the group of pentahydric or hexahydric alcohols (U.S. Pat. No. 6,126,968). The alcohol is typically selected from mannitol, xylitol or sorbitol (U.S. Pat. No. 6,126,968). The composition may further comprise citric acid (U.S. Pat. No. 6,126,968).

(R)-PAI itself may be prepared, for example, according to the process described in Example 6B of WO 95/11016.

EXPERIMENTAL DETAILS 2-chloro-AAI, cis-3-chloro-AAI and trans-3-chloro-AAI can be detected by any of the following methods: UV, fluorescence, and mass spectroscopy. In a specific embodiment, the compounds were analyzed by at least two different analytical methods: A GC-MS or HPLC where detection was by either UV, MS or fluorescence.

Examples 1-4 provide the details of the synthesis of the hydrochloride salt of the four chlorinated N-allyl-(R)-aminoindans. Example 5 provides details on the mesylate salts. Analogous methods are used to produce the hydrochloride salt of the corresponding (S) enantiomers as well as the racemic mixture. Other salts are produced by use of the desired acid in the procedure or by neutralizing the HCl salt and treatment with the desired acid and crystallizing the compound in the presence of suitable solvents.

Example 1

Preparation of 2-chloro-(R)-AAI-HCl 1. (R)-PAI base (30 g) and 32% HCl (100 ml) were refluxed for 33 hours (see scheme 2). The reaction mixture was cooled, toluene (150 ml) and water (150 ml) were added and the mixture was stirred for 15 min. The aqueous phase was separated, brought to pH 14 with 47% NaOH and extracted with 150 ml toluene. The organic phase was evaporated to give 36 g dark brown oil which exhibited 3 spots in TLC, two of which were the desired compounds (hexane-4/EA-6,2-Chloro-AAI base: $R_f$=0.67; cis-3-chloro-AAI base: $R_f$=0.33, visualized in UV). The third spot had the same $R_f$ as the starting material (0.47) and it was thus thought to be the starting material. However, when trans-3-chloro-AAI (see below) was synthesized it was determined that both the trans and the starting material have the same $R_f$ values under the TLC conditions used. Subsequent testing revealed that third spot was due mostly to PAI and only trace amounts of the trans isomer were formed.

2. The compounds formed in step 1 were separated by filtering-column chromatography [Aldrichimica Acta, 21(4), 106-107 (1998)]. Thus 15 g of the product of step 1 was separated on 400 g silica (Merck type 9385) with a mixture of hexane-7/EA-3 to give 5.6 g pure (R)-2-chloro-AAI (15% overall yield) and 5.0 g cis-3-chloro-AAI base (13% overall yield for steps 1 and 2).

3. To 6.7 g of 2-chloro-AAI base in 100 ml diethyl ether was added 9 ml of 14.5% HCl/ethanol solution. The reaction mixture was stirred for ½ hr at ambient temperature and ½ hr at 5-10° C. The precipitate was filtered, washed with ether and dried in vacuum at 50° C. to give 7.1 g (90% yield) of the pure compound, m.p.=166-169° C. (see scheme 2).

The compound exhibited satisfactory NMR and IR spectra which confirmed its structure.

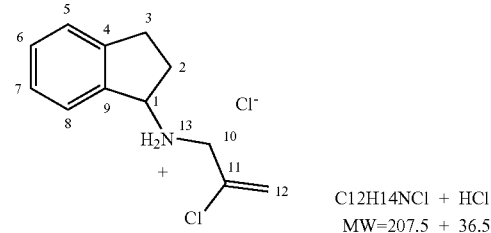

C12H14NCl + HCl
MW=207.5 + 36.5

$^1$H-NMR Spectrum

The $^1$H-NMR spectrum is shown in FIG. 1. NMR Peak assignments are listed below:

| Proton | δ (ppm) | Multiplicity | Coupling Constant (J, Hz) |
|---|---|---|---|
| H1 (1H) | 4.80 | dd | 7, 5 |
| H2 (2H) | 2.33 | m | — |
| H3$^I$ (1H) | 2.82 | ddd | 17, 8, 6 |
| H3$^{II}$ (1H) | 3.18 | dt | 17, 8 |
| H5, H6, H7 (3H) | 7.24-7.25 | m | — |
| H8 (1H) | 7.85 | d | 15 |
| H10 (2H) | 3.83, 3.96 | AB q | 15 |
| H12$^I$ (1H) | 5.65 | s | — |
| H12$^{II}$ (1H) | 5.95 | s | — |
| H13 (2H) | 10.10 | broad s | — |

Mass Spectroscopy (MS)

The mass spectrum of 2-chloro-AAI-HCl was obtained using a Finnigan 4000 Quadropole Low Resolution Mass Spectrometer, operated in electron impact (EI) mode. The electron impact (EI) spectrum exhibits molecular ions at m/z 207 $[M]^{+\bullet}$ and 206 $[M^{+\bullet}\text{-}H]^{+\bullet}$, and characteristic fragments at m/z 171 $[M^{+\bullet}\text{-}HCl]^{+\bullet}$, 132 $[M^{+\bullet}\text{-}C_3H_4Cl]^+$ and 116 $[M^{+\bullet}\text{-}$ C3H6ClN·]+. The EI spectrum is in agreement with the molecular formula of 2-chloro-AAI.

| Elemental Analysis | | | |
|---|---|---|---|
| Calculated | C: 59.03% | H: 6.19% | N: 5.74% |
| Found | C: 58.93% | H: 6.20% | N: 5.68% |

These results correspond to the molecular formula.

FT-IR Spectrum

Figure 2:
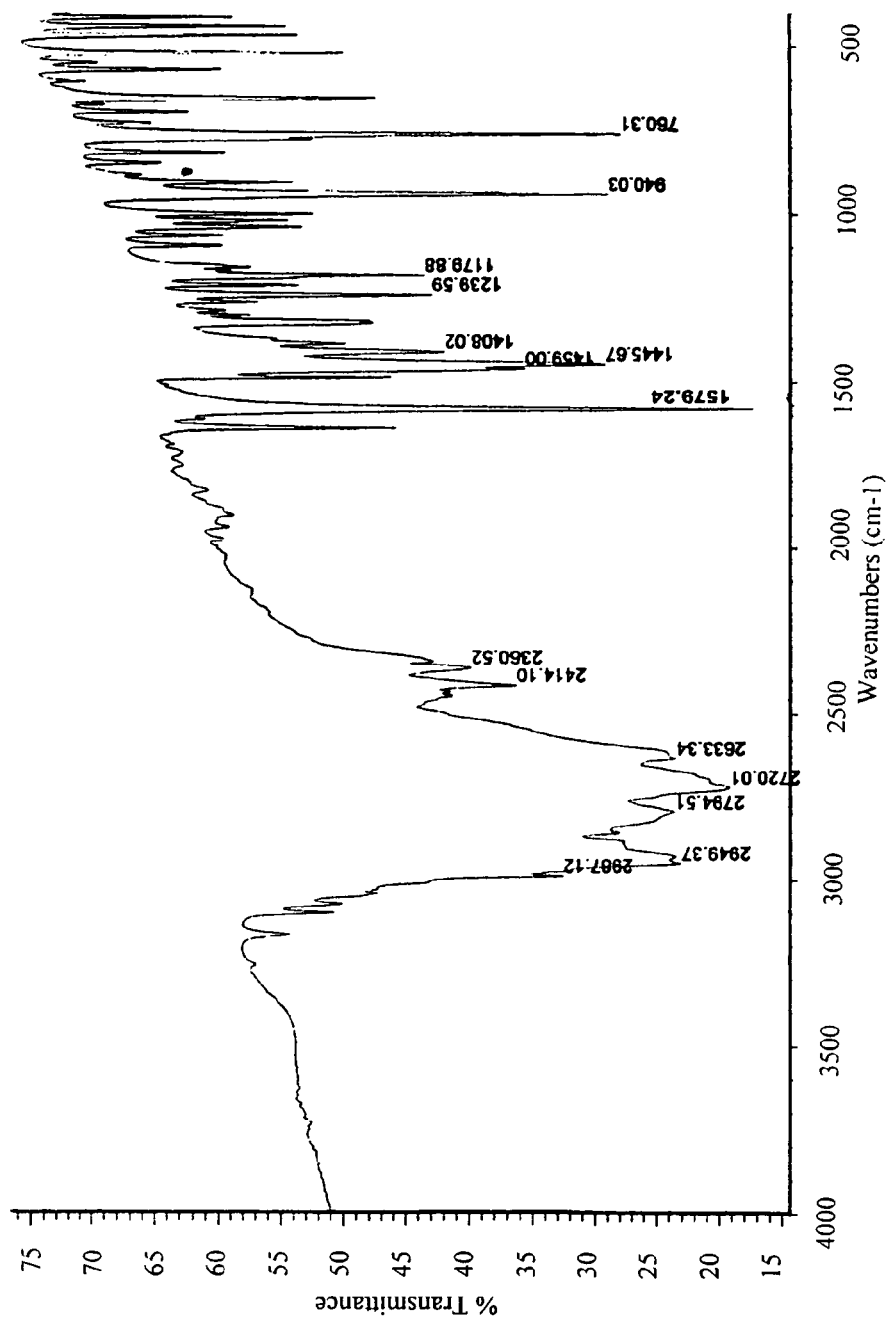
FIG. 2 Infrared spectrum (IR) of a sample of N-2-propene-1-yl-2-chloroaminoindan hydrochloride in KBr, measured with a Nicolet Avatar 320 FT-IR apparatus. The IR spectrum of a KBr pellet at a concentration of about 2% exhibits a typical absorption band at 1579 cm$^{-1}$ (Cl-substituted alkenyl group).
Figure 3:
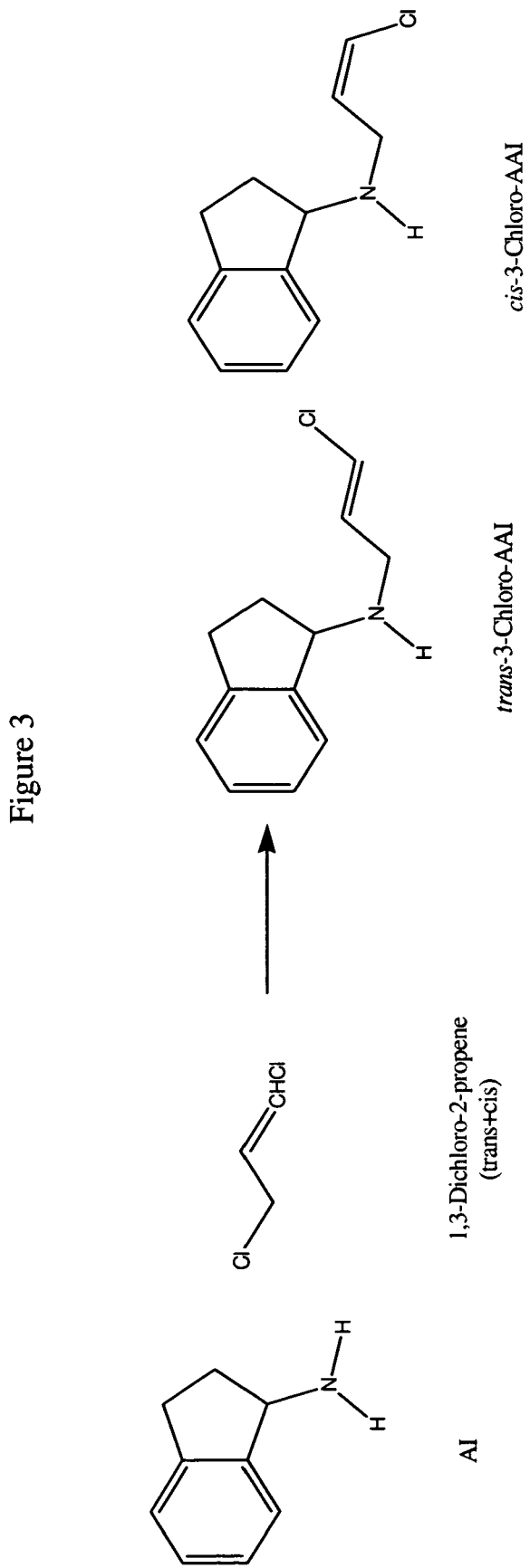
FIG. 3 Scheme 1—preparation of trans-3-Chloro-AAI and cis-3-Chloro-AAI.
Figure 4:
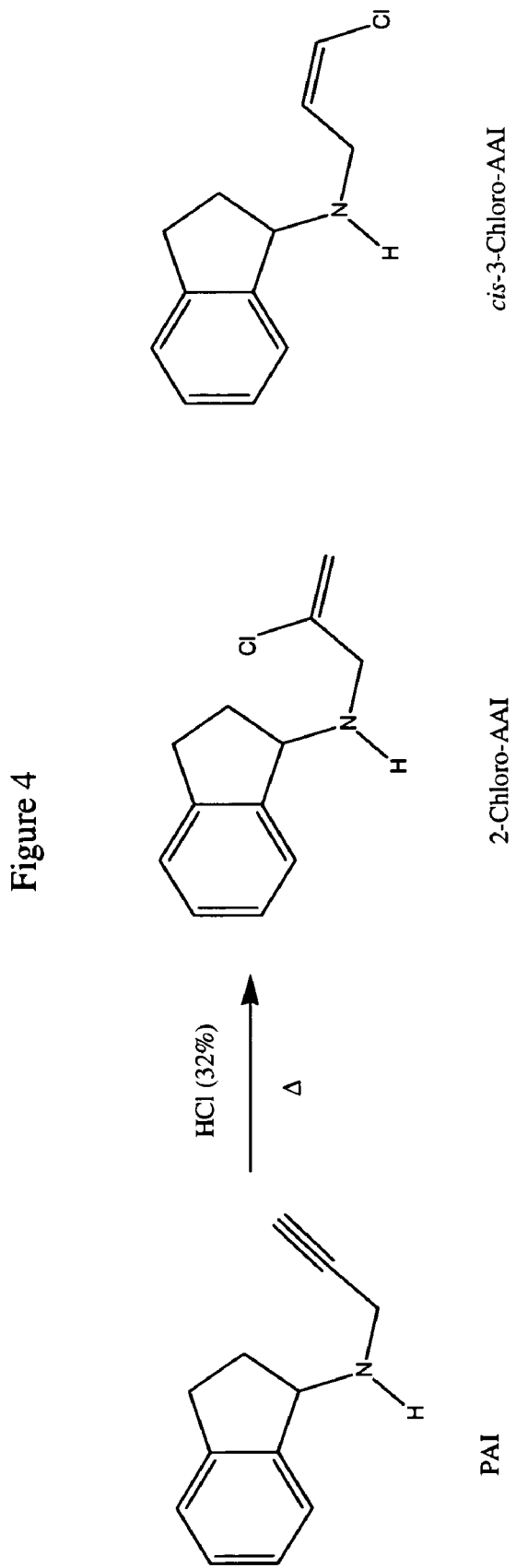
FIG. 4 Scheme 2—preparation of 2-Chloro-AAI and cis-3-Chloro-AAI.
Figure 5:
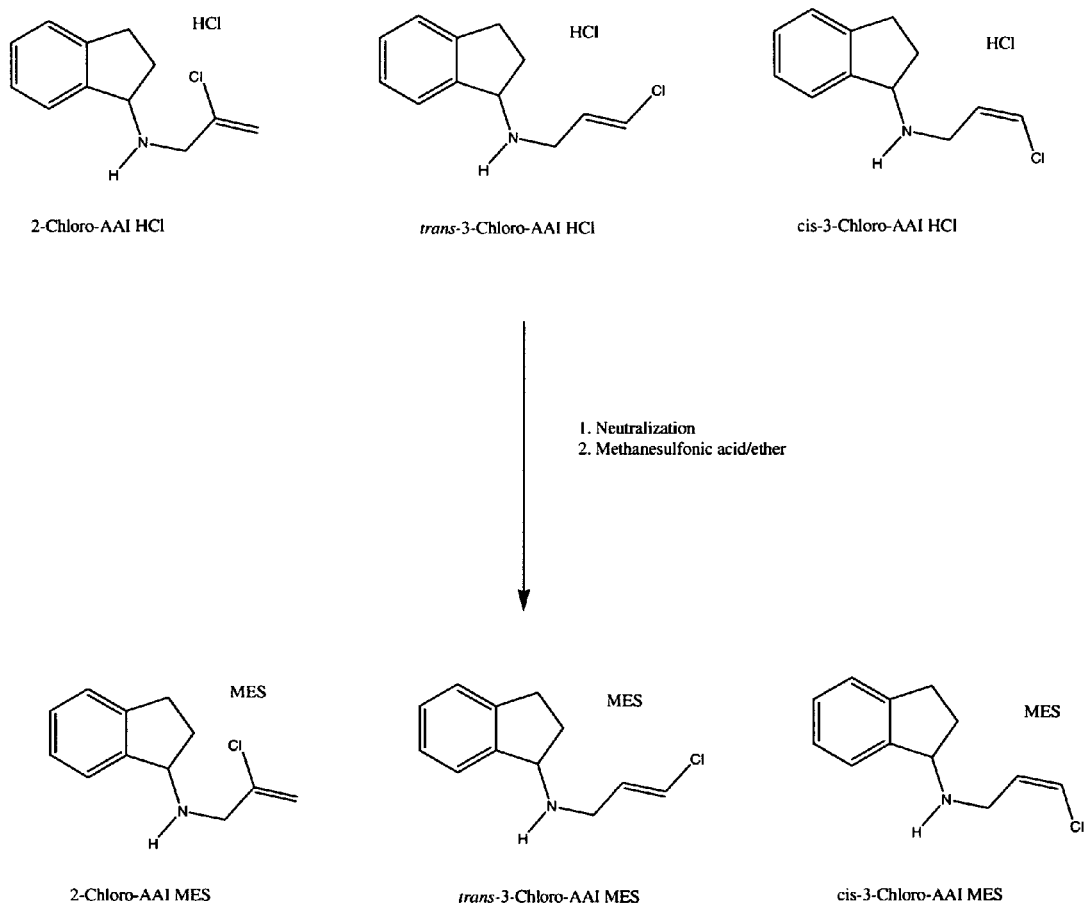
FIG. 5 Scheme 3—preparation of 2-Chloro-AAI MES, trans-3-Chloro-AAI MES and cis-3-Chloro-AAI MES.

The infrared (FT-IR) spectrum of 2-chloro-AAI-HCl is shown in FIG. 2.

Example 2

Preparation of (1,2,3) $^{13}$C-2-chloro-AAI-HCl

A mixture of (1,2,3) $^{13}$C-aminoindan (420 mg, 3.08 mmol) and potassium carbonate (633 mg, 4.57 mmole) in 5 ml of acetonitrile was heated to 60-65° C. and 2,3-dichloro-1-propene (422 μl, 4.57 mmole) was added in one portion. Heating at 60-65° C. was continued overnight after which was added 20 ml of water. The resulting mixture was extracted twice with 20 ml of toluene, the combined extract dried over magnesium sulfate and the solvents evaporated under reduced pressure. The product was purified by column chromatography on silica gel eluting with hexane:ethylacetate (2:1). The combined fractions were isolated, dissolved in ether and treated with ethanolic HCl solution to give the title compound as a white solid after cooling and washing with ether and drying in vacuo (495 mg, 65% yield). The NMR spectrum of this compound was identical to the unlabelled compound of Example 1.

The (1,2,3) $^{13}$C-aminoindan starting material for $^{13}$C-2-Cl-AAI was prepared in seven steps starting with (1,2)-$^{13}$C-phenyl acetic acid using standard chemistry reactions familiar to one skilled in the art. The third $^{13}$C-labelled carbon was introduced with K$^{13}$CN as shown in the following reaction to an aminoindan reference standard, except that the mass spectrograph (ESI) had [M+H]+=137.

| Elemental Analysis | | | | |
|---|---|---|---|---|
| Calculated | C: 59.51% | H: 6.12% | N: 5.67% | Cl: 28.70% |
| Found | C: 58.47% | H: 6.12% | N: 5.54% | Cl: 28.80% |

Mass Spectroscopy (m/e):

M+1=211

M−HCl=175

$C_9H_9$=120

Example 3

Preparation of trans-3-chloro-AAI-HCl

1. A 250 ml round bottom flask equipped with a mechanical stirrer and nitrogen inlet was charged with (R)-AI (10 g, 75 mmol), K$_2$CO$_3$ (10.36 g, 75 mmol) and 26 ml N,N-dimethylacetamide. The reaction mixture was heated to 60° C. and 1,3-dichloropropene (8.35 ml, 0.8 eq., Aldrich 40, 373-3, tech., 80%, mixture of isomers) in toluene (9 ml) were added dropwise within 10 min. After another 4.5 hr of stirring the reaction mixture was cooled and 60 ml water and 30 ml toluene were added. The aqueous phase was separated and extracted again with 30 ml toluene. The combined toluene extracts were washed with 50 ml water, then 50 ml water were added and the pH was adjusted to 2.5 with 6N H$_2$SO$_4$. The water phase was separated, 50 ml toluene was added and the pH was adjusted to 6.5. The organic phase was separated, the water phase was extracted with another portion of toluene (30 ml), the toluene extracts were combined and evaporated to give 12.2 g (78%) crude products. TLC (hexane-4/EA-6) showed 2 main products: trans-3-chloro-AAI, R$_F$=0.47; cis-3-chloro-AAI, R$_F$=0.33 (see scheme 1).

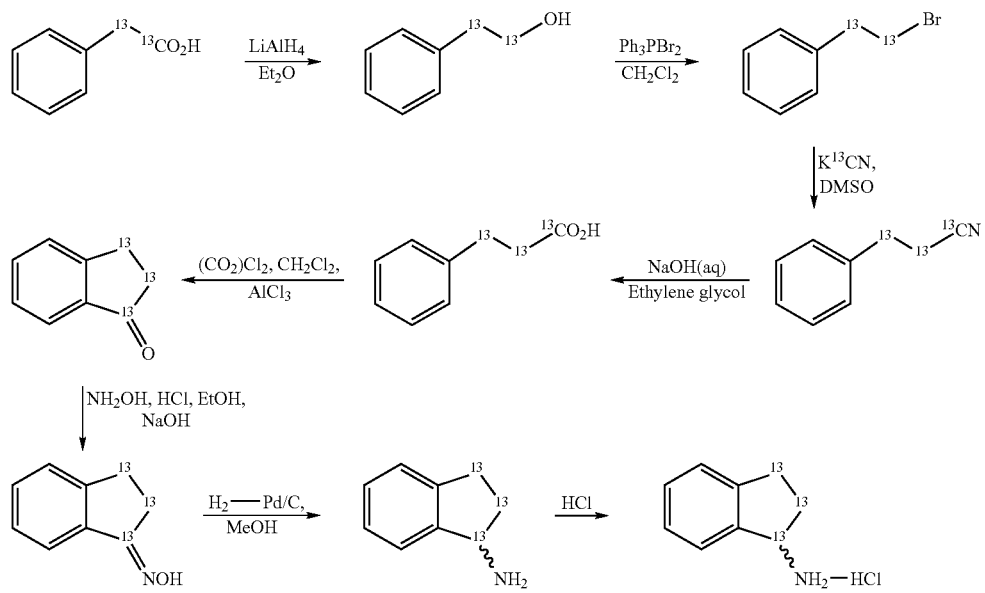

(1,2,3) $^{13}$C-aminoindan was isolated in 51% overall yield and had identical chromatographic and spectrographic properties 2. The separation of trans-3-chloro-AAI from the 12.2 g crude cis/trans mixture was done by filtering-column chromatography over 400 g silica (Merck type 9385) with an eluent composed of EA/hexane (3/7). The yield of pure trans-3-chloro-AAI was 4.5 g (29% overall yield of steps 1 and 2).

3. To 4.5 g of trans-3-chloro-AAI base (from step 2) in 80 ml diethyl ether was added 14.5% HCl/ethanol solution. The reaction mixture was stirred for ½ hr at ambient temperature and ½ hr at 5-10° C. The precipitate was filtered, washed with ether and dried in vacuum at 50° C. to give 4.9 g (94% yield) of the pure compound, m.p.=192-195° C. (see scheme 1). The compound exhibited satisfactory NMR and MS spectra which confirmed its structure.

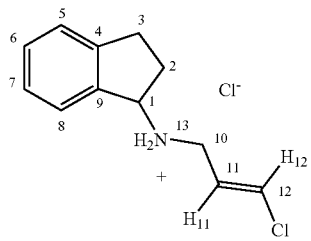

NMR peak assignments are listed below

| Proton | δ (ppm) | Multiplicity |
|---|---|---|
| H1 (1H) | 4.75 | dd |
| H2a (1H) | 2.24 | m |
| H2b (1H) | 2.40 | m |
| H3$^I$ (1H) | 2.86 | ddd |
| H3$^{II}$ (1H) | 3.18 | dt |
| H5, H6, H7 (3H) | 7.24-7.35 | m |
| H8 (1H) | 7.81 | d |
| H10 (2H) | 3.76, 3.78 | m |
| H11 (1H) | 6.70 | dt |
| H12 (1H) | 6.30 | dd |
| H13 (2H) | 10.10 | broad s |

Example 4

Preparation of cis-3-chloro-AAI-HCl

Steps 1 and 2 of Example 1 (see scheme 2) or Example 3 (see scheme 1) can be followed in preparation of cis-3-chloro-AAI. Then, to 5.0 g of cis-3-chloro-AAI base in 90 ml diethyl ether was added 7 ml of 14.5% HCl/ethanol solution. The reaction mixture was stirred for ½ hr at ambient temperature and ½ hr at 5-10° C. The precipitate was filtered, washed with ether and dried in vacuum at 50° C. to give 5.3 g (90% yield) of the pure compound, m.p.=164-166° C. The compound exhibited satisfactory NMR and MS spectra which confirmed its structure.

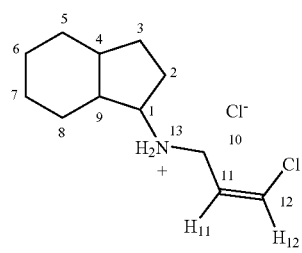

NMR peak assignments are listed below

| Proton | δ (ppm) | Multiplicity |
|---|---|---|
| H1 (1H) | 4.75 | dd |
| H2a (1H) | 2.24 | m |
| H2b (1H) | 2.40 | m |
| H3$^I$ (1H) | 2.86 | ddd |
| H3$^{II}$ (1H) | 3.18 | dt |
| H5, H6, H7 (3H) | 7.24-7.35 | m |
| H8 (1H) | 7.81 | d |
| H10 (2H) | 3.76, 3.78 | AB q |
| H11 (1H) | 6.70 | dt |
| H12 (1H) | 6.30 | dd |
| H13 (2H) | 10.10 | broad s |

Example 5

Preparation of the Mesylate Salts

The hydrochloride salts of the three chlorinated N-allyl aminoindans prepared in examples 1, 3, and 4 were neutralized, the bases separated, dissolved in ether (8 volumes) and cooled to 5° C. Methanesulfonic acid was added and the reaction mixture was stirred for another hour, filtered, washed and dried to give the mesylate salts (88-96% yield, see scheme 3).

2-Chloro-AAI-MES was obtained in 96% yield, m.p.=120-123° C. and exhibited satisfactory NMR and MS spectra which confirmed its structure.

cis-3-Chloro-AAI-MES was obtained in 93% yield, m.p.=116-118° C. and exhibited satisfactory NMR and MS spectra which confirmed its structure.

trans-3-Chloro-AAI-MES was obtained in 88% yield, m.p.=77-80° C. and exhibited satisfactory NMR and MS spectra which confirmed its structure.

Example 6

Testing for Presence of Chlorinated N-allyl Aminoindan By-Products in the Manufacture of PAI-HCl N-(2-chloroallyl)-1-(R)-aminoindan, cis-N-(3-chloroallyl)-1-(R)-aminoindan, trans-N-(3-chloroallyl)-1-(R)-aminoindan, N-(2-chloroallyl)-1-(S)-aminoindan, cis-N-(3-chloroallyl)-1-(S)-aminoindan and trans-N-(3-chloroallyl)-1-(S)-aminoindan are useful as reference standards to detect trace amounts of each of the compounds as a potential impurity in a drug product. Under specific conditions, for example, 2-Chloro-AAI and cis-3-chloro-AAI can be formed from (R)-PAI. Similarly, the (S) enantiomers of the compounds can be formed from (S)-PAI. U.S. Pat. No. 5,532,415 (PCT Application Publication No. WO 95/11016) and U.S. Pat. No. 6,277,886 (PCT Application Publication No. WO 98/02152) disclosed (R)-PAI and (S)-PAI, respectively, their preparation, and various pharmaceutically acceptable salts thereof. Detection methods include the following:

A) GC-MS Method: Using a suitable instrument (e.g., HP-5890 Series II) fitted with a fused silica capillary column with helium carrier gas, samples are detected with a mass selective HP-5971 (EI) detector in the single ion monitoring mode monitoring peaks (for example) with m/z: 172, 206 and 208. Temperatures and flow rates are adjusted to achieve system suitability.

B) HPLC-UV Method: Using a suitable column (e.g., Lichrosphere 60 RP column) peaks are monitored with UV detection at 210 nm or fluorescence excitation at 260 nm (emission at 290 nm).

C) LC/MS:MS Method: Using a suitable instrument (e.g., Agilent 1100 with an Applied Biosystem MDS Sciex API 4000 detector equipped with a turbo ion spray interface) set to detect minute quantities of the claimed compounds. In general, Multiple Reaction Mode detection is used for the ions: 208/117, 211/120, 208/117, 172/117.

A sample of PAI-HCl was injected into an HPLC system equipped with two different detection modes, with eluent A followed by injections of markers and spiked samples, and the results are presented in Table 1:

TABLE 1

| | peaks | | | | | | | |
|---|---|---|---|---|---|---|---|---|
| | rrt 1.58 | | rrt 1.86 | | rrt 1.97 | | rrt 2.13 | |
| Substance | UV | Fl. | UV | Fl. | UV | Fl. | UV | Fl. |
| PAI | + | + | + | − | − | − | + | + |
| PAI + trans 3- | + | + | + | − | ++ | ++ | + | + |
| PAI + cis 3-Cl | + | + | + | − | − | − | ++ | ++ |
| PAI + 2-Cl | ++ | n.d. | + | n.d. | − | n.d. | + | n.d. |
| PAI + indanone | + | + | ++ | − | − | − | + | + |
| trans 3-Cl | − | − | − | − | + | + | − | − |
| cis 3-Cl | − | − | − | − | − | − | + | + |
| 2-Cl | + | n.d. | − | n.d. | − | n.d. | − | n.d. |
| indanone | − | − | + | − | − | − | − | − |

− no response in the specified retention time
n.d. not determined
+ response in the specified retention time
++ increased response due to spiking According to these results, 2-chloro-AAI, cis 3-chloro-AAI and indanone were present in the tested sample.

The same samples were subsequently injected into the HPLC system with eluent B and the following results were obtained (Table 2):

TABLE 2

| | peaks | | | | | | | |
|---|---|---|---|---|---|---|---|---|
| | rrt 1.70 | | rrt 1.90 | | rrt 2.10 | | rrt 2.44 | |
| Substance | UV | Fl. | UV | Fl. | UV | Fl. | UV | Fl. |
| PAI | + | + | − | − | + | − | + | + |
| PAI + trans 3-Cl | + | + | − | − | ++ | ++ | + | + |
| PAI + cis 3-Cl | + | + | − | − | + | − | ++ | ++ |
| PAI + 2-Cl | ++ | n.d. | − | n.d. | + | n.d. | + | n.d |
| PAI + indanone | + | + | ++ | − | + | − | + | + |
| trans 3-Cl | − | − | − | − | + | + | − | − |
| cis 3-Cl | − | − | − | − | − | − | + | + |
| 2-Cl | + | n.d. | − | n.d. | − | n.d. | − | n.d. |
| indanone | − | − | + | − | − | − | − | − |

− response in the specified retention time
++ increased response due to spiking
− no response in the specified retention time
n.d. not determined These results show the presence of 2-chloro-AAI, cis-3-chloro-AAI and an unidentified peak. The presence of the trans-3-chloro-AAI can be ruled out since the response of the trans-3-chloro-AAI related peak was achieved only by UV detection and not by fluorescence in spite of the positive fluorimetric characteristics of the molecule.

A summary of the results obtained by the HPLC system is shown in Table 3:

TABLE 3

| | Eluent A | | Eluent B | |
|---|---|---|---|---|
| Substance | UV | Fl. | UV | Fl. |
| trans 3-Cl | — | — | v | — |
| cis 3-Cl | v | v | v | v |
| 22-Cl | v | n.d. | v | n.d. |
| indanone | v | x | — | x | v present in the specified analytical method
— absent in the specified analytical method
x non fluorescent molecule
n.d. not determined A peak which does not appear in one of the systems in spite of the molecule's ability to absorb UV or emit fluorescence radiation negates the presence of its corresponding substance. Hence, it can be concluded that the 2-chloro-AAI and the cis-3-chloro-AAI are the only chloro containing by-products in this sample.

Three additional samples of PAI-HCl were analyzed as described above. Only 2-chloro-AAI and cis-3-chloro-AAI were identified in these samples. However, in a fourth sample, traces of trans 3-chloro-AAI were also identified.

Accordingly, the fourth sample and one of the earlier samples were further analyzed by GC-MS. The detection was performed using single ion monitoring mode and the results obtained confirmed that the fourth sample contained all three chlorinated N-allyl aminoindans (2-Cl, cis and trans 3-Cl) while the previous sample contained only the first and second impurities.

Example 7

Analysis of Rasagiline formulations

Rasagiline was formulated as a tablet in two different formulations and DW (double weight) as shown in Table 4 below.

TABLE 4

| | Strength | | |
|---|---|---|---|
| | 0.5 mg | 1.0 mg | DW |
| Formulation Code Ingredient | Quantity per Tablet [mg] | | |
| Rasagiline Mesylate | 0.78* | 1.56** | 1.56** |
| Pregelatinized Starch | 10.0 | 10.0 | 20.0 |
| Talc | 2.0 | 2.0 | 4.0 |
| Mannitol | 79.62 | 78.84 | 159.24 |
| Starch | 10.0 | 10.0 | 20.0 |
| Colloidal Anhydrous Silica | 0.6 | 0.6 | 1.2 |
| Stearic Acid | 2.0 | 2.0 | 4.0 |
| Total Weight per Tablet [mg] | 105.0 | 105.0 | 210.0 |

*0.78 mg rasagiline mesylate is equivalent to 0.5 mg rasagiline base
**1.56 mg rasagiline mesylate is equivalent to 1.0 mg rasagiline base Drug product formulations were analyzed for 2-Chloro-AAI after storage under various conditions. Representative results for formulations using the sensitive LC/MS/MS method are summarized in Table 5.

TABLE 5

Representative results of 2-Chloro-AAI measured in formulated Rasagiline Drug Product packaged in HDPE containers or blisterpacks

| Dose (mg) | Container | Storage conditions | | | 2-ClAAI (ppm) |
|---|---|---|---|---|---|
| 1 | Blister-ALU-ALU | 6 M | 40° C. | 75 RH | 10.2 |
| 0.5 | Blister-ALU-ALU | 6 M | 40° C. | 75 RH | 9.3 |
| 1 | Blister-ALU-ALU | 6 M + 5 M | 40° C. | 75 RH | 8.4 |
| 0.5 | Blister-ALU-ALU | 6 M | 40° C. | 75 RH | 5.3 |
| 2 | Blister-ALU-ALU | 6 M | 40° C. | 75 RH | 4.3 |
| 1 | Blister-ALU-ALU | 5 M | 40° C. | 75 RH | 3.5 |
| 2 | Blister-ALU-ALU | 6 M + 5 M | 40° C. | 75 RH | 2.8 |
| 2 | Blister-ALU-ALU | 5 M | 40° C. | 75 RH | 2.4 |
| 0.5 | Blister-ALU-ALU | 29 M | 25° C. | 60 RH | 1.1 |
| 1 | 60 cc | 4 M | 40° C. | 75 RH | <1 ppm |
| 40.5 | Blister-ALU-ALU | 29 M | 25° C. | 60 RH | <1 ppm |
| 0.5 | Blister-ALU-ALU | 29 M | 25° C. | 60 RH | <1 ppm |
| 1 | Blister-ALU-ALU | 11 M | 30° C. | 60 RH | <1 ppm |
| 0.5 | 30 cc | 39 M | 25° C. | 60 RH | <1 ppm |
| 1 | 60 cc | 6 M | 40° C. | 75 RH | <1 ppm |
| 1 | 60 cc | 6 M | 40° C. | 75 RH | <1 ppm |
| 1 | 60 cc | 6 M + 5 M | 40° C. | 75 RH | <1 ppm |
| 1 | 30 cc | 6 M + 5 M | 40° C. | 75 RH | <1 ppm |
| 0.5 | 30 cc | 39 M | 25° C. | 60 RH | <QL |
| 0.5 | 30 cc | 39 M | 25° C. | 60 RH | <QL |
| 1 DW | 30 cc | 39 M | 25° C. | 60 RH | <QL |
| 1 DW | 30 cc | 39 M | 25° C. | 60 RH | <QL |
| 1 DW | 30 cc | 39 M | 25° C. | 60 RH | <QL |
| 1 DW | 30 cc | 39 M | 25° C. | 60 RH | <QL |
| 0.5 | 30 cc | 40 M | 25° C. | 60 RH | <QL |
| 0.5 | 30 cc | 40 M | 25° C. | 60 RH | <QL |
| 1 | 60 cc | 6 M | 40° C. | 75 RH | <QL |
| 1 DW | 60 cc | 5 M | 40° C. | 75 RH | <QL |
| 1 DW | 60 cc | 5 M | 40° C. | 75 RH | <QL |
| 1 DW | 60 cc | 5 M | 40° C. | 75 RH | <QL |
| 0.5 | 30 cc | 39 M | 25° C. | 60 RH | <QL |
| 0.5 | 30 cc | 39 M | 25° C. | 60 RH | <QL |
| 0.5 | 30 cc | 39 M | 25° C. | 60 RH | <QL |
| 1 DW | 30 cc | 39 M | 25° C. | 60 RH | <QL |
| 1 DW | 30 cc | 39 M | 25° C. | 60 RH | <QL |
| 0.5 | 30 cc | 40 M | 25° C. | 60 RH | <QL |
| 0.5 | 30 cc | 40 M | 25° C. | 60 RH | <QL |
| 1 DW | 60 cc | 4 M | 40° C. | 75 RH | <QL |
| 2 | 30 cc | 6 M | 40° C. | 75 RH | <QL |
| 1 DW | 60 cc | 5 M | 40° C. | 75 RH | <QL |
| 1 DW | 60 cc | 5 M | 40° C. | 75 RH | <QL |
| 1 DW | 60 cc | 5 M | 40° C. | 75 RH | <QL |
| 1 DW | 60 cc | 5 M | 40° C. | 75 RH | <QL |
| 1 | 60 cc | 6 M + 5 M | 40° C. | 75 RH | <QL |
| 1 | 60 cc | 6 M + 5 M | 40° C. | 75 RH | <QL |
| 2 | 30 cc | 6 M + 5 M | 40° C. | 75 RH | <QL |
| 0.5 | 30 cc | 40 M | 25° C. | 60 RH | <DL |
| 0.5 | 30 cc | 40 M | 25° C. | 60 RH | <DL |
| 1 DW | Blister-ALU-ALU | 18 M | 25° C. | 60 RH | <DL |
| 1 DW | 30 cc | 28 M | 25° C. | 60 RH | <DL |
| 1 DW | 30 cc | 28 M | 25° C. | 60 RH | <DL |
| 0.5 | Blister-ALU-ALU | 6 M | 30° C. | 60 RH | <DL |
| 2 | Blister-ALU-ALU | 11 M | 30° C. | 60 RH | <DL |
| 1 DW | 60 cc | 4 M | 40° C. | 75 RH | <DL |
| 1 DW | 60 cc | 4 M | 40° C. | 75 RH | <DL |
| 2 | 30 cc | 6 M | 40° C. | 75 RH | <DL |
| 1 DW | 60 cc | 5 M | 40° C. | 75 RH | <DL |
| 2 | 60 cc | 6 M + 5 M | 40° C. | 75 RH | <DL |
| 2 | 60 cc | 6 M + 5 M | 40° C. | 75 RH | <DL |
| 1 | Blister-ALU-ALU | 11 M | 25° C. | 60 RH | <DL |
| 1 | Blister-ALU-ALU | 5 M | 30° C. | 60 RH | <DL |
| 2 | Blister-ALU-ALU | 5 M | 30° C. | 60 RH | <DL |
| 1 DW | 60 cc | 4 M | 40° C. | 75 RH | <DL |
| 2 | 60 cc | 6 M + 5 M | 40° C. | 75 RH | <DL |
| 1 DW | 30 cc | 5 M | 25° C. | 60 RH | <DL |
| 1 DW | 30 cc | 5 M | 25° C. | 60 RH | <DL |
| 1 DW | 30 cc | 5 M | 25° C. | 60 RH | <DL |
| 1 DW | Blister-ALU-ALU | 5 M | 25° C. | 60 RH | <DL |
| 1 DW | Blister-ALU-ALU | 5 M | 25° C. | 60 RH | <DL |
| 1 DW | 30 cc | 5 M | 25° C. | 60 RH | <DL |
| 1 DW | Blister-ALU-ALU | 5 M | 25° C. | 60 RH | <DL |
| 1 DW | 30 cc | 3 M | 25° C. | 60 RH | <DL |
| 1 DW | 30 cc | 3 M | 25° C. | 60 RH | <DL |
| 1 | Blister-ALU-ALU | 5 M | 25° C. | 60 RH | <DL |

(DW indicates a double weight formulation. RH is relative humidity.)
(The 2 mg dose is formulated like the other dose forms, except with more active.)

Observations

2-Chloro-AAI was not observed as an impurity in the drug substance. In some cases after 6 months storage at 40° C. and 75% relative humidity in a blister pack, 2-Chloro-AAI was observed at levels as high as 8-10 ppm.

Discussion

It has been observed that under certain conditions (e.g. 80° C.-100° C., presence of a chloride ion source and low pH), the triple bond of rasagiline in rasagiline mesylate is susceptible to chlorination to form two of the possible chlorinated allyl aminoindans (Cl-AAI'S): N-2-propene-1-yl-2-chloro-(R)-aminoindan and N-2-propene-1-yl-3-chloro-cis-(R)-aminoindan. N-2-propene-1-yl-3-chloro-trans-(R)-aminoindan was not formed in rasagiline mesylate drug product under any of the tested conditions. However, trace amounts of the trans isomer were detected in one batch of (R)-PAI-HCl as noted above. This high degree of stereospecificity was confirmed by independent synthesis of trans-3-chloro-AAI.

Miniscule amounts of 2-Cl-AAI may potentially be generated during the manufacture of rasagiline if any of the reagents contain chloride. Thus, unless the proper precautions are exercised rasagiline may be contaminated with these two chlorinated impurities. Similarly, the formulation excipients must be chosen with low chloride content in order to limit potential sources of chloride ions to avoid the production of 2-Cl-AAI.

The other chlorinated degradant (cis-3-Cl-AAI) is formed more readily than 2-Cl-AAI and under certain conditions it is also useful to monitor the presence of cis-3-Cl-AAI in order to alert one to the presence of 2-Cl-AAI.

In order to minimize the formation of 2-Cl-AAI in the rasagiline mesylate drug product, potential sources of chloride ions during the drug substance synthesis were further limited by replacing the propargylation agent propargyl chloride with propargylbenzene sulfonate, and by limiting the chloride ion content in methanesulfonic acid, which is used in the last reaction step, to not more than 500 ppm.

In addition, during the formulation development of the drug product, a special effort was made to select excipients with low chloride content in order to limit potential sources of chloride ions. The content of 2-Cl-AAI was determined in the drug product at release and during the stability studies (limited to not more than 0.0030%, i.e. 30 ppm) using GC/MS. In view of the fact that 2-Cl-AAI is a potential degradation product of rasagiline as described above, a sensitive screening method is needed to monitor the levels of 2-Cl-AAI in the production of rasagiline. In order to address this need, the subject invention provides a sensitive gas chromatography method to monitor the levels of the 2-Cl-AAI in the rasagiline drug substance and drug product. Detection is conducted by mass spectroscopy under SIM conditions which provides high selectivity of the GC/MS method. Screening may also be accomplished using high performance liquid chromatography (HPLC) equipped with a UV/fluorescence detector or a MS:MS detector.

What is claimed is:

1. A process of manufacturing N-2-propene-1-yl-2-chloro-aminoindan, N-2-propene-1-yl-3-chloro-cis-aminoindan, or an enantiomer or a salt of any one thereof, comprising reacting N-propargyl-1-aminoindan with hydrochloric acid in the presence of a solvent so as to produce N-2-propene-1-yl-2-chloro-aminoindan, N-2-propene-1-yl-3-chloro-cis-aminoindan, or an enantiomer or a salt of any one thereof.

2. The process of claim 1, wherein the solvent is a mixture of toluene and water.

3. A process of manufacturing (1,2,3) $^{13}$C—N-2-propene-1-yl-2-chloro-aminoindan or an enantiomer or a salt thereof, comprising:
   a) heating a mixture of (1,2,3) $^{13}$C-aminoindan and a base in a first solvent,
   b) adding 2,3-dichloro-1-propene to produce (1,2,3) $^{13}$C—N-propargyl-1-aminoindan,
   c) reacting the (1,2,3) $^{13}$C—N-propargyl-1-aminoindan of step b) with HCl in the presence of a second solvent to produce the compound.

4. The process of claim 3, wherein the base is $K_2CO_3$.

5. The process of claim 3, wherein the first solvent is acetonitrile.

6. The process of claim 3, wherein the second solvent is ether.

7. The process of any of claims 1-6, further comprising recovering the compound so produced.

8. The process of claim 1, wherein the product manufactured is N-2-propene-1-yl-2-chloro-aminoindan, or an enantiomer or a salt thereof.

9. The process of claim 1, wherein the product manufactured is N-2-propene-1-yl-3-chloro-cis-aminoindan, or an enantiomer or a salt thereof.

10. A process of manufacturing (1,2,3) $^{13}$C—N-2-propene-1-yl-2-chloro-aminoindan, or an enantiomer or a salt thereof, comprising reacting (1,2,3) $^{13}$C—N-propargyl-1-aminoindan with hydrochloric acid in the presence of a solvent so as to produce (1,2,3) $^{13}$C—N-2-propene-1-yl-2-chloro-aminoindan, or an enantiomer or a salt thereof.

11. The process of claim 10, wherein the solvent is a mixture of toluene and water.

* * * * *